(12) United States Patent
Matsumoto et al.

(10) Patent No.: US 7,811,779 B2
(45) Date of Patent: Oct. 12, 2010

(54) METHOD OF MULTIQUANTIFICATION FOR CHOLESTEROL OF LOW-DENSITY LIPOPROTEIN

(75) Inventors: Keiko Matsumoto, Niigata (JP); Hiroshi Matsui, Niigata (JP)

(73) Assignee: Denka Seiken Co., Ltd., Tokyo (JP)

( * ) Notice: Subject to any disclaimer, the term of this patent is extended or adjusted under 35 U.S.C. 154(b) by 746 days.

(21) Appl. No.: 10/594,898

(22) PCT Filed: Mar. 30, 2005

(86) PCT No.: PCT/JP2005/006162

§ 371 (c)(1),
(2), (4) Date: Sep. 29, 2006

(87) PCT Pub. No.: WO2005/095639

PCT Pub. Date: Oct. 13, 2005

(65) Prior Publication Data

US 2007/0207515 A1    Sep. 6, 2007

(30) Foreign Application Priority Data

Mar. 31, 2004  (JP) .............................. 2004-106006

(51) Int. Cl.
*C12Q 1/60* (2006.01)
*C12Q 1/44* (2006.01)
*C12Q 1/28* (2006.01)

(52) U.S. Cl. .............................. 435/11; 435/19; 435/28

(58) Field of Classification Search ........................ None
See application file for complete search history.

(56) References Cited

U.S. PATENT DOCUMENTS

| | | | |
|---|---|---|---|
| 4,378,429 A * | 3/1983 | Modrovich | ................. 435/11 |
| 5,925,534 A | 7/1999 | Miki et al. | |
| 6,057,118 A | 5/2000 | Nakamura et al. | |
| 6,194,164 B1 | 2/2001 | Matsui et al. | |

FOREIGN PATENT DOCUMENTS

| | | |
|---|---|---|
| EP | 1 114 870 A1 | 7/2001 |
| EP | 1 577 398 A | 9/2005 |
| JP | 2001-124780 | 5/2001 |
| JP | 2001-224397 | 8/2001 |
| WO | WO 97/45553 A1 | 12/1997 |
| WO | WO 98/47005 A1 | 10/1998 |
| WO | WO 00/17388 A1 | 3/2000 |
| WO | WO 00/73797 A2 | 12/2000 |

OTHER PUBLICATIONS

Hiroshi Matsui, "LDL-Cholesterol to So-Cholesterol no Multi Teiryoho", Japanese Journal of Clinical Laboratory Automation, Aug. 2003, 28(4), p. 380.
Takashi Kanno, "Koshikessho LDL-Cholesterol no Chokusetsu Sokuteiho", Current Therapy, 16(1), 1998, pp. 146-150.
Takashi Matsui, "Atarashii LDL Cholesterol Chokusetsuho Shiyaku (LDL-EX) no. Kaihatsu", Seibutsu Shiryo Bunseki, 21(5), 1998, pp. 361-366.
Database WPI Week 200473 Thompson Scientific, London, GB; AN 2004-748067 & XP002506349 & WO 2004/087945 A (Denka Seiken KK) Oct. 14, 2004 Abstract.

* cited by examiner

*Primary Examiner*—Vera Afremova
(74) *Attorney, Agent, or Firm*—Stephen A. Bent; Foley & Lardner LLP

(57) ABSTRACT

Provided is a method of stabilizing a reagent that allows simultaneous quantification of LDL cholesterol and total cholesterol by a single measurement by suppressing spontaneous color development thereof. A method of quantification for cholesterol in low density lipoprotein and total cholesterol in a biological sample by the single measurement comprises a first step of treating lipoproteins other than low density lipoprotein in the biological sample to generate hydrogen peroxide and a second step of converting the hydrogen peroxide obtained in the first step to a quinone dye and treating remaining low density lipoprotein and converting generated hydrogen peroxide to the quinone dye, where the quinone dye is not formed in the first step, and cholesterol in low density lipoprotein and total cholesterol are quantified from the amount of the quinone dye formed in the second step by the single measurement.

4 Claims, 3 Drawing Sheets

METHOD OF MULTIQUANTIFICATION FOR CHOLESTEROL OF LOW-DENSITY LIPOPROTEIN

TECHNICAL FIELD

The present invention relates to a method for simultaneously measuring cholesterol in low density lipoprotein and total cholesterol as analytes in biological samples, and particularly to a method that makes it possible to stabilize liquid reagents used for the measurement.

BACKGROUND ART

Low density lipoprotein (hereinafter, referred to as "LDL") plays a major role in cholesterol transport in blood, and particularly, cholesterol deposited on the walls of blood vessels in atherosclerosis is mainly derived from LDL. An increase in LDL cholesterol is a major risk factor of arteriosclerotic diseases, and its selective quantification is clinically useful. The total cholesterol measurement involves measurement of cholesterol in all lipoproteins such as chylomicron (CM), very low density lipoprotein (VLDL), LDL, and high density lipoprotein (HDL) and is still a main item of lipid test.

Conventional methods for quantifying LDL cholesterol include a method of quantification from two operations of fractionation and cholesterol determination and a method of quantification by calculation based on the values of total cholesterol, HDL cholesterol, and triglycerides according to the Friedewald equation.

For fractionation, there are methods such as ultracentrifugation, precipitation, and immunological technique. These methods require a process for treatment of a sample by ultracentrifugation or filtration and have been difficult to be widely used at laboratory testing sites in view of convenience and cost effectiveness. The calculation method based on the Friedwald equation is limited in its use and associated with accuracy problem because individual differences are not taken into consideration.

Recently, a method of quantification for LDL cholesterol that does not require fractionation has been reported (JP-Patent Publication (Kokai) No. 11-318496 A (1999)) and is currently being used at testing sites as a laboratory testing reagent. This method comprises a first step in which cholesterol in lipoproteins other than LDL in a sample is selectively eliminated ("eliminated" means that ester type cholesterol is degraded and the degradation product is made undetectable in a second step) and a second step in which LDL cholesterol is quantified.

Despite the fact that the reagent for LDL cholesterol measurement described above is a clinically useful reagent, the conventional measurement of total cholesterol is widely performed, and the reagent has not come into wide use because of the reason that LDL cholesterol levels can be determined using the Friedewald equation and so forth. However, there is a problem in LDL cholesterol levels determined by the Friedewald equation as described above, and accurate measurement of LDL cholesterol levels is clinically significant. Hence, it has been desired to further improve the reagent, thereby allowing the reagent for LDL cholesterol measurement of high clinical significance to become widely used.

On the other hand, a method in which cholesterol in HDL and total cholesterol as well as cholesterol in LDL and total cholesterol are sequentially measured by a single measurement was disclosed (JP-Patent Publication (Kohyo) No. 2003-501630 A). In this method, a sample is put in a tube, allowed to form a complex between non-HDL cholesterol in the sample and an anti-apoB antibody, and measured for lipoprotein in uncomplexed form, namely, HDL. Then the complex is dissociated with a surfactant, and remaining non-HDL cholesterol is enzymically measured. By summing the two measurement values, total cholesterol level is found. In the case of LDL cholesterol, a similar reaction method is used, in which an anti-apoA-I or anti-apoA-II antibody is used rather than the anti-apoB antibody at the time of complex formation. HDL cholesterol, LDL cholesterol, and total cholesterol are conventionally widely measured in medical checkup and the like, and the simultaneous measurement of HDL cholesterol, LDL cholesterol, and total cholesterol has been of significance.

Patent document 1: JP-Patent Publication (Kokai) No. 11-318496 A (1999)

Patent document 2: JP-Patent Publication (Kohyo) No. 2003-501630 A

DISCLOSURE OF THE INVENTION

The object of the present invention is to provide a method of stabilization to suppress spontaneous color development of a reagent that makes it possible to simultaneously quantify LDL cholesterol and total cholesterol by a single measurement. This method is useful as a multiple quantification method in which quantified values of a plurality of items can be obtained in a single measurement.

In light of the importance of accurate measurement of LDL cholesterol attracting recent attention and the conventionally known importance of total cholesterol measurement, the present inventors studied diligently to establish a simultaneous measurement system of LDL cholesterol and total cholesterol.

The present inventors have previously developed a method capable of simultaneous measurement of LDL cholesterol and total cholesterol (Japanese Patent Application No. 2002-362970, PCT/JP03/15995). This method comprises allowing cholesterol esterase and cholesterol oxidase to act on lipoproteins in the presence of a surfactant that acts on lipoproteins other than LDL, measuring cholesterol in the lipoproteins other than LDL by converting generated hydrogen peroxide to a quinone dye, subsequently adding a surfactant that acts at least on LDL, allowing the cholesterol esterase and cholesterol oxidase to act on the remaining LDL, and measuring LDL cholesterol by converting generated hydrogen peroxide to the quinone dye, where total cholesterol value can be calculated by summing the above two measurement values. This method was effective as a multiple quantification method in which quantified values of a plurality of items can be obtained in a single measurement. In this method, however, components to produce the quinone dye are present in a first reagent in a state of a liquid reagent for use, and thus, the reagent is oxidized by air to give a problem of spontaneous color development and lacks stability as a liquid reagent.

Hence, the present inventors diligently studied the stabilization of the reagent that makes it possible to quantify LDL cholesterol and total cholesterol simultaneously by a single measurement and found a method in which LDL cholesterol and total cholesterol are consistently measured by suppressing spontaneous color development in the reagent for use in a method of simultaneous quantification for LDL cholesterol and total cholesterol by a single measurement.

In the previous method of quantification, procedures from the enzymic reaction of cholesterol in lipoproteins other than LDL in a sample to the detection of cholesterol were performed in the first step. However, in the present method of quantification, the procedures were improved so as to enable to detect the enzymic reaction of cholesterol in lipoproteins other than LDL, which occurs in the first step, at an early stage of the second step and to detect the enzymic reaction of LDL cholesterol after the following stages.

FIG. 1 depicts the principle of the present invention. As shown in FIG. 1, the method of the present invention comprises two steps. In the first step, hydrogen peroxide is generated by a reaction based on cholesterol in lipoproteins other than LDL in a sample. In the second step, a change in absorbance of the reaction solution due to the hydrogen peroxide generated in the first step takes place, subsequently a reaction based on cholesterol in LDL takes place, and a change in absorbance of the reaction solution due to the reaction is measured. The amount of the total change in absorbance in the second step corresponds to total cholesterol, and the amount of change in absorbance with respect to the amount of hydrogen peroxide generated in the second step corresponds to the amount of LDL cholesterol. By changing analytical conditions at the time of measuring this change in absorbance on an automatic analyzer, measurement of multiple items can be simultaneously performed by a single measurement.

In the conventional method of multiple quantification, a plurality of reagent compositions involved in quinone dye formation were integrated in a first reagent used in the first step of the measurement. On the other hand, in the present method, since the quinone dye is formed only in the second step, the plurality of reagent compositions involved in the quinone dye formation could be separated into a first reagent used in the first step and a second reagent used in the second step, and the spontaneous color development caused by air oxidation of the reagent could be suppressed. Since suppression of the spontaneous color development in the reagent became possible, the reagent could be stabilized, thereby making it possible to consistently measure cholesterol.

When the method of the present invention is performed using an automatic analyzer on which various measurement conditions can be set, one measurement condition to set the analyzer in analysis of multiple items is that total cholesterol is quantified from total change in absorbance in the second step. Another measurement condition is that LDL cholesterol is quantified from the difference of absorbances between two points after addition of the second reagent (at the point after a rapid change in absorbance right after adding the second reagent and at the final point of the reaction) in the second step.

That is, the present invention is as follows.

[1] A method of quantification for cholesterol in low density lipoprotein and total cholesterol in a biological sample by a single measurement, comprising:
a first step of treating lipoproteins other than low density lipoprotein in the biological sample to generate hydrogen peroxide; and
a second step of converting the hydrogen peroxide obtained in the first step to a quinone dye and treating remaining low density lipoprotein and converting generated hydrogen peroxide to the quinone dye,
wherein the quinone dye is not formed in the first step, and cholesterol in low density lipoprotein and total cholesterol are quantified from the amount of the quinone dye formed in the second step by a single measurement;

[2] The method of [1] wherein reagent compositions involved in the formation of the quinone dye comprise 4-aminoantipyrine, a phenolic or anilinic hydrogen donor compound, and peroxidase; either one of 4-aminoantipyrine or the phenolic or anilinic hydrogen donor compound is added in the first step; and the reagent compositions not added in the first step is added in the second step;

[3] The method of [1] or [2], wherein cholesterol esterase and cholesterol oxidase are allowed to act on lipoproteins other than low density lipoprotein in the biological sample in the presence of a surfactant that acts on lipoproteins other than low density lipoprotein to generate hydrogen peroxide in the first step; and the cholesterol esterase and cholesterol oxidase are allowed to act on low density lipoprotein in the biological sample in the presence of a surfactant that acts at least on low density lipoprotein to generate hydrogen peroxide in the second step;

[4] The method of any of [1] to [3], wherein in the second step, the hydrogen peroxide obtained in the first step is converted to the quinone dye; the surfactant that acts at least on low density lipoprotein is added to the measurement system; the cholesterol esterase and cholesterol oxidase are allowed to act on low density lipoprotein remaining in the measurement system; and the generated hydrogen peroxide is measured by converting to the quinone dye;

[5] The method of any of [1] to [4], wherein the amounts of cholesterol present in low density lipoprotein and total cholesterol present in the biological sample are simultaneously measured based on two values where the total amount of change in absorbance in the second step serves as a measurement value that reflects the amount of total cholesterol present and the amount of change in absorbance with respect to the amount of the hydrogen peroxide generated in the second step serves as a measurement value that reflects the amount of cholesterol present in low density lipoprotein;

[6] The method of any of [1] to [5], wherein the change in absorbance in the second step shows a biphasic increase in which there are a rapid increase right after adding a second reagent and a subsequent moderate increase; and cholesterol in low density lipoprotein is quantified from the amount of the latter moderate change in absorbance;

[7] The method of any of [1] to [6], wherein total cholesterol is quantified from the total amount of change in absorbance in the second step;

[8] The method of any of [1] to [7], wherein analysis is performed by a single measurement under different measurement conditions using an automatic analyzer for clinical chemistry testing;

[9] A method of stabilizing a liquid reagent in a method of quantification for cholesterol in low density lipoprotein and total cholesterol in a biological sample by a single measurement including a first step of adding a first reagent to treat lipoproteins other than low density lipoprotein in the biological sample to generate hydrogen peroxide and a second step of adding a second reagent to convert the hydrogen peroxide generated in the first step to a quinone dye and to treat remaining low density lipoprotein to generate hydrogen peroxide and convert to the quinone dye, comprising:
containing either 4-aminoantipyrine or a phenolic or anilinic hydrogen donor compound that is a reagent composition involved in the formation of the quinone dye in the first reagent added in the first step; and
containing reagent compositions not contained in the first reagent among 4-aminoantipyrine, the phenolic or anilinic hydrogen donor compound, and peroxidase in the second reagent;

[10] A method of stabilizing a liquid reagent in a method of any of [1] to [8], comprising:
containing either 4-aminoantipyrine or a phenolic or anilinic hydrogen donor compound that is a reagent composition involved in the formation of a quinone dye in a first reagent added in a first step; and containing reagent compositions not contained in the first reagent among 4-aminoantipyrine, the phenolic or anilinic hydrogen donor compound, and peroxidase in a second reagent;

[11] The method of [9] or [10], wherein a surfactant that acts on lipoproteins other than low density lipoprotein, cholesterol esterase, and cholesterol oxidase are further contained in the first reagent; and a surfactant that acts at least on low density lipoprotein is contained in the second reagent;

[12] A kit to perform a method of quantification for cholesterol in low density lipoprotein and total cholesterol in a biological sample by a single measurement including a first step of adding a first reagent to treat lipoproteins other than low density lipoprotein in the biological sample to generate hydrogen peroxide and a second step of adding a second reagent to convert the hydrogen peroxide generated in the first step to a quinone dye and to treat remaining low density lipoprotein to generate hydrogen peroxide and convert to the quinone dye, comprising:

containing either 4-aminoantipyrine or a phenolic or anilinic hydrogen donor compound that is a reagent composition involved in the formation of the quinone dye in the first reagent; and containing reagent compositions not contained in the first reagent among 4-aminoantipyrine, the phenolic or anilinic hydrogen donor compound, and peroxidase in the second reagent;

[13] The kit of [12], wherein a surfactant that acts on lipoproteins other than low density lipoprotein, cholesterol esterase, and cholesterol oxidase are further contained in the first reagent; and a surfactant that acts at least on low density lipoprotein is contained in the second reagent.

By the method of the present invention, the reagent used in the method of quantifying LDL cholesterol and total cholesterol simultaneously in a single measurement can be stably kept in a liquid state such that spontaneous color development due to air oxidation does not occur. Further, LDL cholesterol and total cholesterol can be consistently measured in a single measurement.

The present specification encompasses the contents described in the specification or the drawings, or both of Japanese Patent Application No. 2004-106006, on which the priority of the present application is based.

BEST MODE FOR CARRYING OUT THE INVENTION

Figure 1:
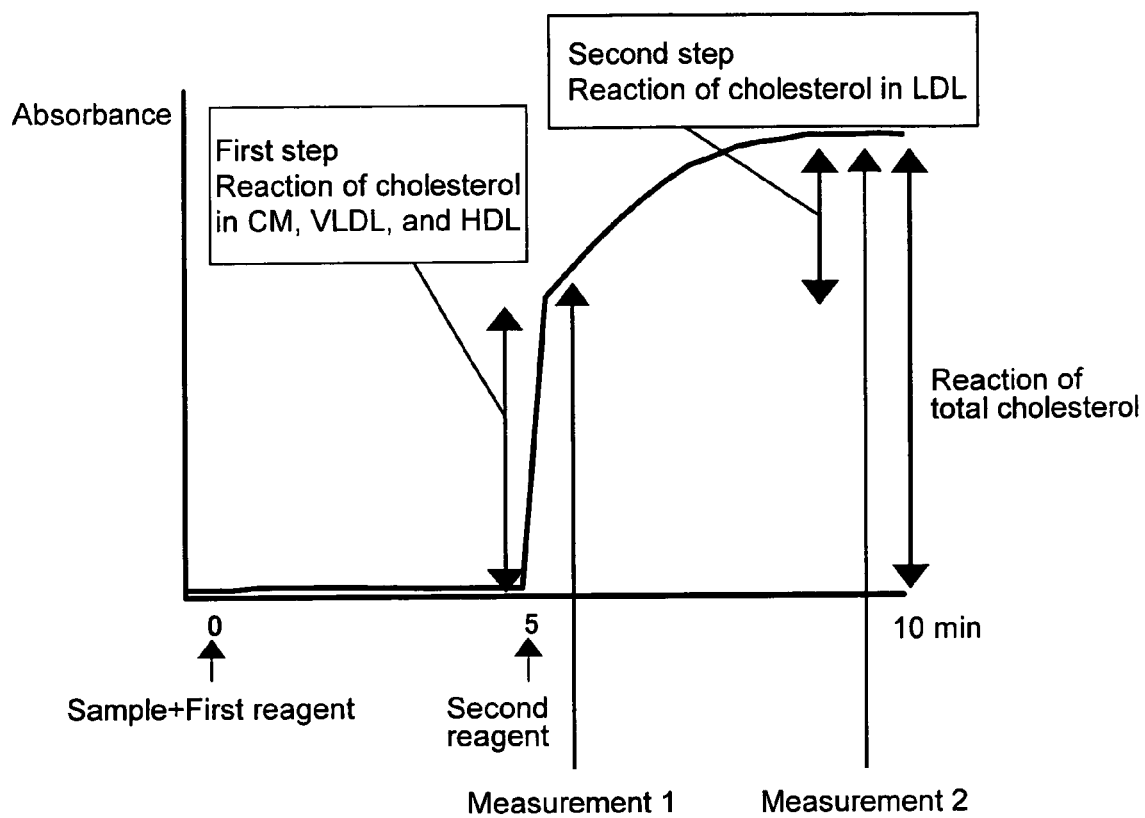
FIG. 1 is a diagram showing the principle of a method of multiple quantification of the present invention.

The present invention is a method of simultaneously measuring cholesterol in LDL and total cholesterol in a biological sample in which cholesterol in LDL and total cholesterol in a biological sample are quantified by a single measurement using absorbances of a dye formed by treatment of lipoproteins as an indicator. Further, the present invention is a method in which the stability of a reagent or a reagent composition is enhanced by preventing spontaneous color development of the reagent caused by air oxidation and consistent results can be obtained even when the reagent is left for a long period of time. In the method of the present invention, hydrogen peroxide is generated by treating lipoproteins in a biological sample, then the hydrogen peroxide is converted to a quinone dye, and the absorbance of the quinone dye is measured, thereby measuring cholesterol contained lipoproteins in the biological sample. The method of the present invention comprises a first step in which lipoproteins other than LDL in a biological sample are treated to generate hydrogen peroxide and a second step in which the hydrogen peroxide obtained in the first step is converted to the quinone dye and the remaining LDL is treated to generate hydrogen peroxide and this hydrogen peroxide is converted to the quinone dye. That is, in the method of the present invention, lipoproteins other than LDL and LDL are treated in different steps, respectively, and the conversion of hydrogen peroxide generated by the treatments to the quinone dye and the detection of the formed quinone dye are carried out in a single step. Here, the treatment of lipoproteins refers to treating lipoproteins with a surfactant and enzymes. When lipoproteins are treated with a surfactant, cholesterol in lipoproteins is released. When this cholesterol is treated with enzymes (cholesterol esterase and cholesterol oxidase), hydrogen peroxide is generated. That is, the treatment of lipoproteins includes a series of treatments in which cholesterol is released from lipoproteins and further hydrogen peroxide is generated from cholesterol. Further, the treatment of cholesterol refers to generating hydrogen peroxide by the treatment of released cholesterol with the enzymes. The generated hydrogen peroxide is subsequently converted to the quinone dye with peroxidase. In the present invention, "reagent" refers to an article containing reagent compositions, and "reagent compositions" refers to substances such as surfactant and enzyme that constitute the reagent.

In the first step, lipoproteins other than LDL in a biological sample are treated with a surfactant and enzymes to generate hydrogen peroxide. Since a set of reagent compositions involved in the generation of the quinone dye is not contained in a first reagent used in the first step, generated hydrogen peroxide is not converted to the quinone dye. In the second step, LDL is treated with a surfactant and enzymes, and hydrogen peroxide is newly generated by the reaction. When a second reagent used in the second step is added to the measurement system, the set of reagent compositions involved in the generation of the quinone dye become contained in the measurement system, whereby lipoprotein in LDL is treated, and at the same time, the reaction to convert hydrogen peroxide present in the measurement system to the quinone dye takes place. When the second step is initiated, hydrogen peroxide generated from cholesterol in lipoproteins other than LDL that has been formed in the first step is present in the measurement system, and the hydrogen peroxide is converted to the quinone dye at the same time as the initiation of the second step. On the other hand, hydrogen peroxide generated by the treatment of LDL in the second step is converted to the quinone dye concurrently with its generation. The hydrogen peroxide generated by the treatment of LDL in the second step increases with time as the treatment of cholesterol with the enzymes progresses. Since the hydrogen peroxide generated by the treatment of LDL in the second step is converted to the quinone dye, the quinone dye also increases with time. The change in absorbance due to quinone dye right after the initiation of the second step reflects the amount of hydrogen peroxide generated in the first step, that is, the amount of cholesterol present in lipoproteins other than LDL. The change in absorbance due to quinone dye when the second step ends reflects the amount of hydrogen peroxide generated in the first step and an additional amount of hydrogen peroxide generated in the second step, that is, the amount of cholesterol present in LDL. In other words, the total change in absorbance in the second step serves as a measurement value that reflects the amount of total cholesterol present in a biological sample, and a change in absorbance with respect to the amount of hydrogen peroxide generated in the second step serves as a measurement value that reflects the amount of cholesterol present in LDL. Based on these two changes in absorbance, that is, the total change in absorbance in the second step and the change in absorbance with respect to the amount of hydrogen peroxide generated in the second step, cholesterol in LDL and total cholesterol present in the biological sample can be measured at the same time. In the method of the present invention, different reagents are used in the first step and the second step. By elaborate grouping of the components of the two reagents, mainly reagent compositions involved in the formation of quinone dye, stabilization of the reagents themselves can be achieved and consistent results can also be obtained in the method of cholesterol measurement. The reagent compositions refer to components of a reagent composition necessary for carrying out a chemical reaction such as reagents involved in a specific chemical reaction or buffer solution, or both. In the method of the present invention, stabilization of a liquid reagent supplied in liquid can be achieved. Hydrogen peroxide generated by the treatment of cholesterol forms a colored quinone (quinone dye) in the presence of peroxidase, 4-aminoantipyrine, and a phenolic or anilinic hydrogen donor compound. When peroxidase, 4-aminoantipyrine, and the phenolic or anilinic hydrogen donor compound are present in a reagent in a mixed liquid state, the quinone dye is formed with time owing to an effect of air oxidation even when hydrogen peroxide is not present, resulting in spontaneous color development of the reagent. Therefore, the stability of the reagent or the reagent composition for measurement of cholesterol can not be maintained, and the consistency of cholesterol measurement cannot also be guaranteed. In the present invention, all of peroxidase, 4-aminoantipyrine, and a phenolic or anilinic hydrogen donor compound are not allowed to be copresent in one of the two reagents. Only after the two reagents are added finally to the measurement system, all of peroxidase, 4-aminoantipyrine, and the phenolic or anilinic hydrogen donor compound are allowed to be added in the system.

Cholesterol contained in lipoproteins that is the measurement target of the method of the present invention includes ester cholesterol (cholesteryl ester) and free cholesterol. When simply "cholesterol" is referred to in the present specification, the term includes both of these.

Biological samples submitted to the method of the present invention are those that may contain lipoproteins such as HDL, LDL, VLDL, and CM and include, for example, body fluids such as blood, serum, and plasma, and diluted fluids thereof, but are not limited to these. "Lipoproteins other than LDL" refers to HDL, VLDL, CM, and the like.

"Measurement value that reflects the amount of total cholesterol present" or "measurement value that reflects the amount of cholesterol present in LDL" indicates a measurement value obtained when the concentration or absolute amount of cholesterol present in lipoproteins of a biological sample is determined. The measurement method is not particularly limited, and when a value corresponding to the concentration or absolute amount of cholesterol present in lipoproteins of a biological sample, for example, a proportional or inversely proportional value is finally obtained by combining a plurality of measurements, this value is referred to as measurement value. For example, one example of the measurement values is absorbance due to a compound formed by a series of treatments of cholesterol in lipoproteins with specific agents. The measurement value in this case includes an absolute amount as well as a change amount.

For example, the change in absorbance in the second step shown in FIG. 1 is the one in which absorbance arising from converting hydrogen peroxide generated by the treatment in the second step to the quinone dye is added to absorbance arising from converting hydrogen peroxide generated by the treatment in the first step to the quinone dye. In FIG. 1, absorbance that reflects the amount of cholesterol present in LDL is obtained from the amount of change in absorbance (the difference between absorbances obtained by measurement 2 and measurement 1) of the absorbance obtained by measurement 2 in the second step, and this absorbance is the "measurement value that reflects the amount of cholesterol present in LDL". The total absorbance obtained by the measurement 2 in the second step is a value in which the absorbance corresponding to the amount of cholesterol present in LDL is added to the absorbance that reflects the amount of cholesterol present in lipoproteins other than LDL, and this absorbance is the "measurement value that reflects the amount of total cholesterol present". However, in order to obtain an accurate measurement value in practice, the amount of cholesterol is calculated based on the value obtained by subtracting an absorbance before the addition of the second reagent from the absorbance obtained by the measurement 2.

"A single measurement" in the case where two kinds of measurement values are obtained by a single measurement includes a series of continuous treatments until a plurality of necessary measurement values are obtained after submitting a biological sample to the measurement. During the single measurement, a plurality of times of addition of reagents and acquisition of measurement values are included, but separation operation by centrifugation and the like and separation operation by complex formation are not included. Preferably, the measurement is completed at a single time in a single tube or well for measurement.

"The amounts of LDL cholesterol and total cholesterol in a biological sample are simultaneously obtained based on two measurement values" refers to obtaining the concentrations or the absolute values of cholesterol in LDL and total cholesterol by calculation based on two measurement values. For example, the amount of cholesterol present in LDL can be known from the change amount of the measurement value obtained by the measurement 2 in FIG. 1, i.e., the difference between both measurement values of the measurements 1 and 2, and the amount of total cholesterol present can be known from the measurement value obtained by the measurement 2.

The treatment in the first step is carried out by degrading cholesterol by enzymic reactions in the presence of a surfactant that acts on lipoproteins other than LDL. Hydrogen peroxide generated by the treatment is retained up to the second step without being eliminated and detected. A surfactant acts means degradation of lipoproteins by the surfactant to release cholesterol in lipoproteins.

A specific method to selectively react cholesterol contained in lipoproteins other than LDL, i.e., HDL, VLDL, CM, and the like, is as follows.

That is, cholesterol esterase and cholesterol oxidase are allowed to act on lipoproteins in the presence of the surfactant that acts on lipoproteins other than LDL to generate hydrogen peroxide.

The concentration of cholesterol esterase in the reaction solution of the first step is preferably from 0.2 to 2.0 IU/mL, and cholesterol esterase produced originally by a pseudomonad bacterium is effective. Further, the concentration of cholesterol oxidase is preferably from 0.1 to 0.7 IU/mL, and it is preferred to use cholesterol oxidase derived from a bacterium or a yeast.

Preferred examples of the surfactant used in the first step that acts on lipoproteins other than LDL can include polyalkylene oxide derivatives having an HLB value of 13 or more and 15 or less, preferably 13 or more and 14 or less. Examples of the derivatives can include higher alcohol condensates, higher fatty acid condensates, higher fatty acid amide condensates, higher alkylamine condensates, higher alkylmercaptan condensates, alkylphenol condensates, and the like. It should be noted that the calculation method of the HLB value of surfactants is well-known and described, for example, in "Shin Kaimenkasseizai (in Japanese)(New Surfactants)", Hiroshi Horiuchi, 1986, Sankyou Publishing Co., LTD.

Specific preferred examples of polyalkylene oxide derivatives having an HLB value of 13 or more and 15 or less can include polyoxyethylene lauryl ether, polyoxyethylene cetyl ether, polyoxyethylene oleyl ether, polyoxyethylene higher alcohol ether, polyoxyethylene octylphenyl ether, polyoxyethylene nonylphenyl ether, polyoxyethylene benzylphenyl ether, and the like that are compounds having an HLB value of 13 or more and 15 or less. However, polyalkylene oxide derivatives are not limited to these.

As the surfactant used in the first step, for example, Emulgen B66 (product of Kao Corporation) that is a polyoxyethylene derivative and has an HLB value of 13.2 can be named.

The concentration of the surfactant used in the first step is preferably from ca. 0.1 to 10 g/L, more preferably from ca. 0.5 to 5 g/L.

The first step is preferably carried out in a buffer solution at pH 5 to 9, and a buffer solution containing an amine such as Tris buffer, triethanolamine buffer, or Good's buffer is preferred. In particular, Bis-Tris, PIPES, MOPSO, BES, HEPES, and POPSO that are Good's buffers are preferable, and the concentration of the buffer solution is preferably from 10 to 500 mM.

The reaction temperature of the first step is suitably ca. 30 to 40 degrees C., most preferably 37 degrees C. The reaction time (time from the addition of the first reagent to the addition of the second reagent) is ca. 2 to 10 min, and preferably 5 min.

In the method of the present invention, it is desired to carry out the first step in the presence of albumin. The albumin is not limited at all as long as it is albumin, and commercially available albumin such as serum albumin can be preferably used, where fatty acid-free albumin is particularly preferable. The origin of the albumin is not limited at all and may be any animal such as human, bovine, pig, and horse, and particularly, bovine serum albumin that is widely used can be preferably used. The concentration of the albumin in the reaction solution of the first step is preferably from 0.1 to 5.0 g/dL, more preferably from 0.3 to 3.0 g/dL.

As described above, the first reagent used in the first step includes at least a surfactant, cholesterol esterase, and cholesterol oxidase. The reagent may further contain an appropriate buffer and albumin. The reagent used in the first step does not contain all of the reagent compositions involved in the formation of quinone dye but contains either 4-aminoantipyrine or a phenolic or anilinic hydrogen donor compound. Further, the first reagent used in the first step does not contain peroxidase.

In the first step, hydrogen peroxide is generated corresponding to the amount of cholesterol in lipoproteins other than LDL present in a biological sample, and the hydrogen peroxide is carried over to the second step without being eliminated or detected.

In the subsequent second step, the hydrogen peroxide generated from cholesterol in lipoproteins other than LDL that have been treated in the first step is quantified, and cholesterol in LDL remaining at the end of the first step is treated and quantified.

The treatment of cholesterol in LDL is carried out by treating LDL with a surfactant that acts at least on LDL. Cholesterol in LDL generates hydrogen peroxide by the action of the surfactant, cholesterol esterase, and cholesterol oxidase. Here, cholesterol esterase and cholesterol oxidase are contained in the first reagent used in the first step, and those added to the measurement system in the first step may be used. Further, cholesterol esterase and cholesterol oxidase may also be contained in the second reagent used in the second step. The surfactant that acts at least on LDL may be either a surfactant that selectively acts only on LDL or a surfactant that acts on all lipoproteins.

Since the measurement value of LDL is calculated from the amount of change in absorbance after the addition of the second reagent, accuracy of the measurement value is governed by the reaction rate, that is, the reaction intensity of the used surfactant. Therefore, it is preferable to select a surfactant having an appropriate reaction intensity.

Preferred examples of the surfactant that selectively acts only on LDL or acts on all lipoproteins can include polyalkylene oxide derivatives not used in the first reagent. Examples of the derivatives can include higher alcohol condensates, higher fatty acid condensates, higher fatty acid amide condensates, higher alkylamine condensates, higher alkylmercaptan condensates, and alkylphenol condensates.

Specific preferred examples of polyalkylene oxide derivatives can include polyoxyethylene lauryl ether, polyoxyethylene cetyl ether, polyoxyethylene oleyl ether, polyoxyethylene higher alcohol ether, polyoxyethylene octylphenyl ether, polyoxyethylene nonylphenyl ether, polyoxyethylene benzylphenyl ether, and the like that are compounds not used in the first reagent. As the surfactant used in the second step, for example, Polidocanol (Thesit) (product of Roche Diagnostic Corporation) that is a polyoxyethylene lauryl alcohol and has an HLB value of 13.3 is named.

The concentration of the surfactant used in the second step is preferably from ca. 0.1 to 100 g/L, more preferably from ca. 1 to 50 g/L.

Other preferred reaction conditions in the second step are the same as preferred the reaction conditions in the first step. However, in the second step of the method of the present invention, hydrogen peroxide contained in the measurement system that was derived from cholesterol in lipoproteins other than LDL is converted to quinone dye right after the second step is initiated, while cholesterol in LDL generates hydrogen peroxide as the second step progresses, and the hydrogen peroxide is converted to the quinone dye. The increase in absorbance due to the quinone dye formed by the treatment of lipoproteins other than LDL starts at the same time as the addition of the second reagent, progresses at a rapid rate, and ends in a short time. On the other hand, since LDL is treated to generate hydrogen peroxide after the addition of the second reagent and then the quinone dye is formed, the absorbance that reflects the amount of LDL present starts to increase with a certain time lag after the addition of the second reagent, and the rate of the increase is not so high. In other words, the increase in absorbance in the second step shows a biphasic increase consisting of the rapid increase right after initiating the second step and the moderate increase. The initial rapid increase is the increase that reflects the amount of lipoproteins other than LDL present and the subsequent moderate increase is the increase that reflects the amount of LDL present.

Accordingly, it is desirable to terminate the formation of the quinone dye derived from cholesterol in LDL within 30 sec or more and 5 min or less after the addition of the second reagent so that the quinone dye derived from cholesterol in lipoproteins other than LDL and the quinone dye derived from cholesterol in LDL might be measured independently to allow the amount of cholesterol present in LDL to be accurately quantified.

Cholesterol in lipoproteins other than LDL can be quantified by determining hydrogen peroxide generated through the actions of cholesterol esterase and cholesterol oxidase in the first step. Cholesterol in LDL can be quantified by adding a surfactant that acts at least on LDL in the second step and determining hydrogen peroxide generated through the actions of the surfactant and the cholesterol esterase and cholesterol oxidase that have been added in the first step. The determination of hydrogen peroxide can be carried out by a method in which generated hydrogen peroxide is converted, in the presence of peroxidase, to a colored quinone by causing the oxidative condensation between 4-aminoantipyrine and a phenolic or anilinic hydrogen donor compound and measured at a wavelength of 400 to 700 nm. At this time, when the second reagent used in the second step is added to the measurement system, all of the reagent compositions involved in the formation of quinone dye, i.e., peroxidase, 4-aminoantipyrine, and a phenolic or anilinic hydrogen donor compound becomes contained in the measurement system. That is, the second reagent used in the second step contains at least a surfactant that acts on LDL and contains the reagent compositions that are not contained in the first reagent used in the first step among peroxidase, 4-aminoantipyrine, and a hydrogen donor compound (phenolic or anilinic). Further, the second reagent used in the second step may contain any of buffer solution, albumin, cholesterol esterase, and cholesterol oxidase.

The measurement value of absorbance of the quinone dye formed in the reaction of the second step is the one in which absorbance arising from hydrogen peroxide generated in the second step is added to absorbance arising from hydrogen peroxide generated by the reaction in the first step, and indicates the amount of cholesterol present in all lipoproteins in a biological sample. The absorbance obtained by subtracting the absorbance due to hydrogen peroxide arising from the first step from the total absorbance, that is, determination of hydrogen peroxide generated in the second step indicates the amount of cholesterol present in LDL.

Of the hydrogen donor compounds, examples of anilinic hydrogen donor compounds include N-(2-hydroxy-3-sulfopropyl)-3,5-dimethoxyaniline (HDAOS), N-ethyl-N-sulfopropyl-3-methoxyaniline (ADPS), N-ethyl-N-sulfopropylaniline (ALPS), N-ethyl-N-sulfopropyl-3,5-dimethoxyaniline (DAPS), N-sulfopropyl-3,5-dimethoxyaniline (HDAPS), N-ethyl-N-sulfopropyl-3,5-dimethylaniline (MAPS), N-ethyl-N-sulfopropyl-3-methylaniline (TOPS), N-ethyl-N-(2-hydroxy-3-sulfopropyl)-3-methoxyaniline (ADOS), N-ethyl-N-(2-hydroxy-3-sulfopropyl)aniline (ALOS), N-ethyl-N-(2-hydroxy-3-sulfopropyl)-3,5-dimethoxyaniline (DAOS), N-ethyl-N-(2-hydroxy-3-sulfopropyl)-3,5-dimethylaniline (MAOS), N-ethyl-N-(2-hydroxy-3-sulfopropyl)-3-methylaniline (TOOS), N-sulfopropylaniline (HALPS), and the like.

The concentration of peroxidase when hydrogen peroxide is converted to the quinone dye in the reaction solution of the second step is preferably from 0.1 to 3.0 IU/mL, the concentration of 4-aminoantipyrine is preferably from 0.3 to 3.0 mmol/L, and the concentration of the phenolic or anilinic hydrogen donor compound is preferably from 0.5 to 2.0 mmol/L.

Since all of the reagent compositions involved in the formation of the quinone dye become contained in the system when the second reagent is added in the second step, hydrogen peroxide generated in the first step is converted to the quinone dye at an early stage of the second step. At the same time, cholesterol in LDL is subjected to treatment with the surfactant that is contained in the second reagent and acts on LDL and the cholesterol esterase and cholesterol oxidase that are contained in the measurement system to generate hydrogen peroxide. Since the hydrogen peroxide arising from cholesterol in LDL is converted, at the same time as it is formed, to the quinone dye by the action of the reagent compositions involved in the formation of the quinone dye that are contained in the measurement system, the amount of the quinone dye increases with time. Therefore, in the second step, absorbance rapidly increases at the same time as the start of the second step and continues to increase with time as shown in FIG. 1. In a first measurement, the absorbance that increased rapidly is measured. In a second measurement, the absorbance that increased with time is measured. The measurement value of the second measurement reflects the amount of total cholesterol present, and the difference between the measurement value of the second measurement and the measurement value of the first measurement reflects the amount of cholesterol present in LDL.

The time after the addition of the second reagent and before the first measurement, that is, the time required for conversion of hydrogen peroxide generated in the first step to the quinone dye is from 0 to 60 sec, preferably within 30 sec. Further, the time before performing the second measurement, that is, the time required for generating hydrogen peroxide from entire cholesterol present in LDL by the enzymic actions in the second step and converting the generated hydrogen peroxide to the quinone dye is from 1 to 5 min. When the measurement is performed at two points of the first measurement and the second measurement and two measurement values are obtained, the amounts of total cholesterol and cholesterol in LDL can be quantified by calculation according to the calculation process of these two measurement values.

The calculation formulae are shown below.

$$\text{Total cholesterol:} \frac{\Delta AT_{sample} - \Delta AT_{BLK}}{\Delta AT_{STD} - \Delta AT_{BLK}} \times CT_{STD}$$

$$\text{LDL cholesterol:} \frac{\Delta AL_{sample} - \Delta AL_{BLK}}{\Delta AL_{STD} - \Delta AL_{BLK}} \times CT_{STD}$$

$\Delta AT_{sample}$: Amount of change in absorbance determined by subtracting absorbance due to only a sample and the first reagent from absorbance obtained by the measurement 2 of the sample $\Delta AT_{STD}$: Amount of change in absorbance determined by subtracting absorbance due to only a standard sample and the first reagent from absorbance obtained by the measurement 2 of the standard sample $\Delta AT_{BLK}$: Amount of change in absorbance determined by subtracting absorbance due to only a sample and the first reagent from absorbance obtained by the measurement 2 when saline or purified water is used as the sample $CT_{STD}$: Total cholesterol value of the standard sample $\Delta AL_{sample}$: Amount of change in absorbance determined by subtracting absorbance obtained by the measurement 1 of the sample from absorbance obtained by the measurement 2 of the sample $\Delta AL_{STD}$: Amount of change in absorbance determined by subtracting absorbance obtained by the measurement 1 of the standard sample from absorbance obtained by the measurement 2 of the standard sample $\Delta AL_{BLK}$: Amount of change in absorbance determined by subtracting absorbance obtained by the measurement 1 from absorbance obtained by the measurement 2 when saline or purified water is used as a sample $CL_{STD}$: LDL cholesterol value of the standard sample In the method of the present invention, the pathway in which each lipoprotein is treated to form the quinone dye is summarized as follows. It should be noted that the following summarizes the process (treatment) of forming the quinone dye but does not show the reagent compositions.

Treatment of lipoproteins other than LDL

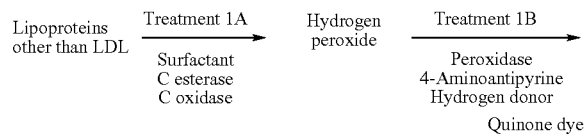

Treatment of LDL

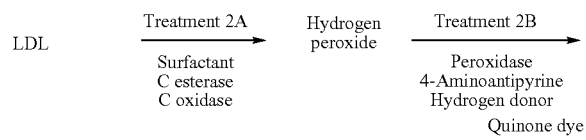

The reagent compositions under each arrow are reagent compositions necessary for each treatment (reaction), where C esterase indicates cholesterol esterase and C oxidase indicates cholesterol oxidase.

Among the above treatments, the treatment 1A is carried out in the first step of the method of the present invention, and the treatment 1B, the treatment 2A, and the treatment 2B are carried out in the second step. In the second step, the treatment 1B is completed at an early stage of the second step, and the treatment 2A and the treatment 2B are carried out throughout the second step.

Preferably, the first step and the second step are continuously carried out in one reaction vessel, and an automatic analyzer automatically measures the amount of change in absorbance in the second step and absorbance at the time of completion of the second step.

The analyzer for use in the method of the present invention is an automatic analyzer having a function to perform a simultaneous analysis method for multiple items in which multiple items can be measured simultaneously. The automatic analyzer includes TBA-30R (Toshiba Corporation), BM1250, 1650, and 2250 (JEOL Ltd.), and the like.

As the function of the analyzer to perform a simultaneous analysis method for multiple items, a first reagent to a fourth reagent can be added in a reaction vessel and also reaction time can be set to 3 to 20 min. Further, since photometric measurements are carried out a plurality of times during reaction time, it is possible to set different measurement times, thereby allowing different time setting for colorimetry and rate analysis as well as combination of colorimetric method and rate method. Still further, simultaneous measurements at different wavelengths can also be performed. The simultaneous measurement of multiple items of the present invention can be achieved by appropriately setting these measurement conditions for analysis.

For the automatic analyzer having a function to perform a simultaneous analysis method for multiple items, a commercially available analyzer can be used.

The present invention further includes a kit to measure cholesterol in LDL and total cholesterol in a biological sample at the same time. The kit of the present invention includes the first reagent and the second reagent. The first reagent contains the surfactant that acts at least on lipoproteins other than LDL, cholesterol esterase, and cholesterol oxidase. The first reagent may further contain the reagent compositions involved in the formation of the quinone dye including peroxidase, 4-aminoantipyrine, and the phenolic or anilinic hydrogen donor compound, but all of peroxidase, 4-aminoantipyrine, and the phenolic or anilinic hydrogen donor compound are not contained at the same time. Still further, peroxidase is not contained, and either one of 4-aminoantipyrine or the phenolic or anilinic hydrogen donor compound is contained. Still further, the first reagent may contain an appropriate buffer solution, albumin, and the like. The second reagent contains the surfactant that acts at least on LDL and additionally reagent compositions that are not contained in the first reagent among the reagent compositions involved in the formation of the quinone dye including peroxidase, 4-aminoantipyrine, and the phenolic or anilinic hydrogen donor compound. The second reagent may further contain an appropriate buffer solution, albumin, and the like. It is possible to measure absorbance of the colored quinone formed by the reaction of the reagent compositions. The kit of the present invention further contains a standard lipoprotein solution of known concentration, a buffer solution, and the like.

EXAMPLES

Hereinafter, the present invention is more specifically explained based on examples. However, the present invention is not limited to the examples described below.

Reagent compositions used in the first step and the second step (first reagent compositions and second reagent compositions, respectively) were prepared so as to have the following compositions, respectively. The reagent compositions corresponding to two measurement systems that have different compositions for the first reagent and the second reagent respectively were prepared.

| Measurement system 1 | |
|---|---|
| First reagent composition | |
| PIPES buffer solution, pH 7.0 | 50 mmol/L |
| 4-Aminoantipyrine | 1.4 mmol/L |
| Cholesterol esterase | 0.6 IU/mL |
| Cholesterol oxidase | 0.5 IU/mL |
| Surfactant, Emulgen B66 (Kao Corp.) | 0.27% |
| Second reagent composition | |
| PIPES buffer solution, pH 7.0 | 50 mmol/L |
| Surfactant, Polidocanol (Thesit) (Roche Diagnostic Corp.) | 1% |
| TOOS | 6 mmol/L |
| POD (peroxidase) | 6.5 IU/mL |
| Measurement system 2 | |
| First reagent composition | |
| PIPES buffer solution, pH 7.0 | 50 mmol/L |

-continued

| | |
|---|---|
| TOOS | 2 mmol/L |
| Cholesterol esterase | 0.6 IU/mL |
| Cholesterol oxidase | 0.5 IU/mL |
| Surfactant, Emulgen B66 (Kao Corp.) | 0.27% |
| Second reagent composition | |
| PIPES buffer solution, pH 7.0 | 50 mmol/L |
| Surfactant, Polidocanol (Thesit) (Roche Diagnostic Corp.) | 1% |
| 4-Aminoantipyrine | 4 mmol/L |
| POD | 6.5 IU/mL |

As control products for evaluation, commercially available reagent for automatic analysis, LDL-EX N (product of Denka Seiken Co., Ltd.) and reagent for automatic analysis T-CHO (S)N (product of Denka Seiken Co., Ltd.) were used.

(Sample)

Fifty-eight human serum samples were prepared.

As the automatic analyzer, TBA-30R (product of Toshiba Corporation) was used.

(Reagent for Simultaneous Analysis of LDL-C and T-CHO (Multi-Reagent))

Measurement Conditions: Automatic Analysis of Multiple Items

After 300 μL of the first reagent pre-warmed to 37 degrees C. was mixed with each 4 μL sample and reacted for 5 min at 37 degrees C., 100 μL of the second reagent was added and reacted further for 5 min. After the addition of the second reagent, absorbance at 600 nm was measured at 30 sec later and 5 min later. The level of LDL cholesterol (LDL-C) was calculated from the amount of change in absorbance between 30 sec and 5 min after the addition of the second reagent, and the level of total cholesterol (T-CHO) was calculated from the amount of change in absorbance after the addition of the second reagent. At this time, the amount of change in absorbance due to saline (hereinafter, referred to as blank) and the amount of change in absorbance when a sample of known concentration was used as a standard sample were measured in advance, and "the amount of change in absorbance per mg/dL" was calculated from the difference of these two values for each of LDL-C and T-CHO. Then, the sample was measured, and the amount of change in absorbance obtained by subtracting blank from the measured amount of change in absorbance was compared with "the amount of change in absorbance per mg/dL" to calculate the concentrations of LDL-C and T-CHO, respectively.

Figure 2:
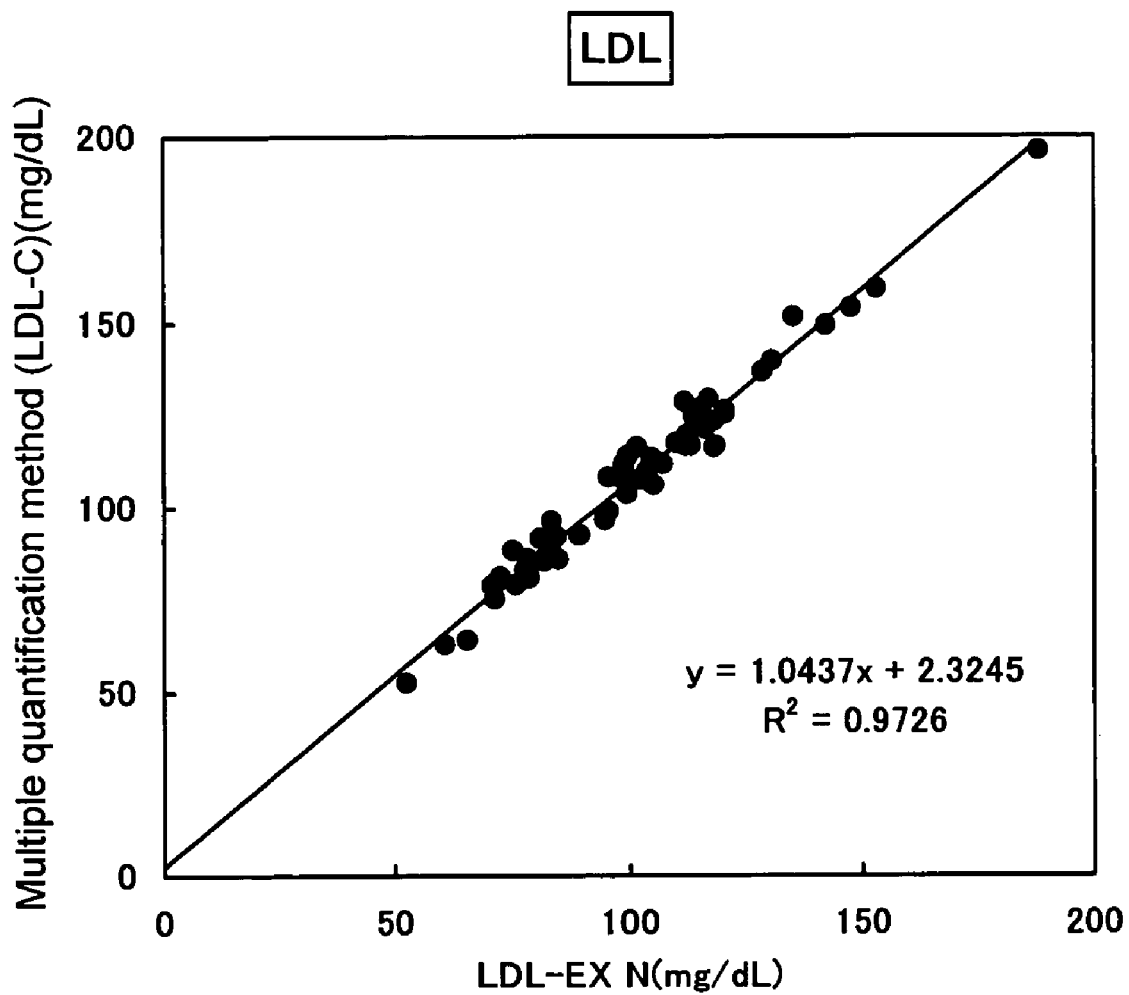
FIG. 2 is a diagram showing the correlation between cholesterol levels in LDL measured by the method of multiple quantification of the present invention and cholesterol levels in LDL measured independently.
Figure 3:
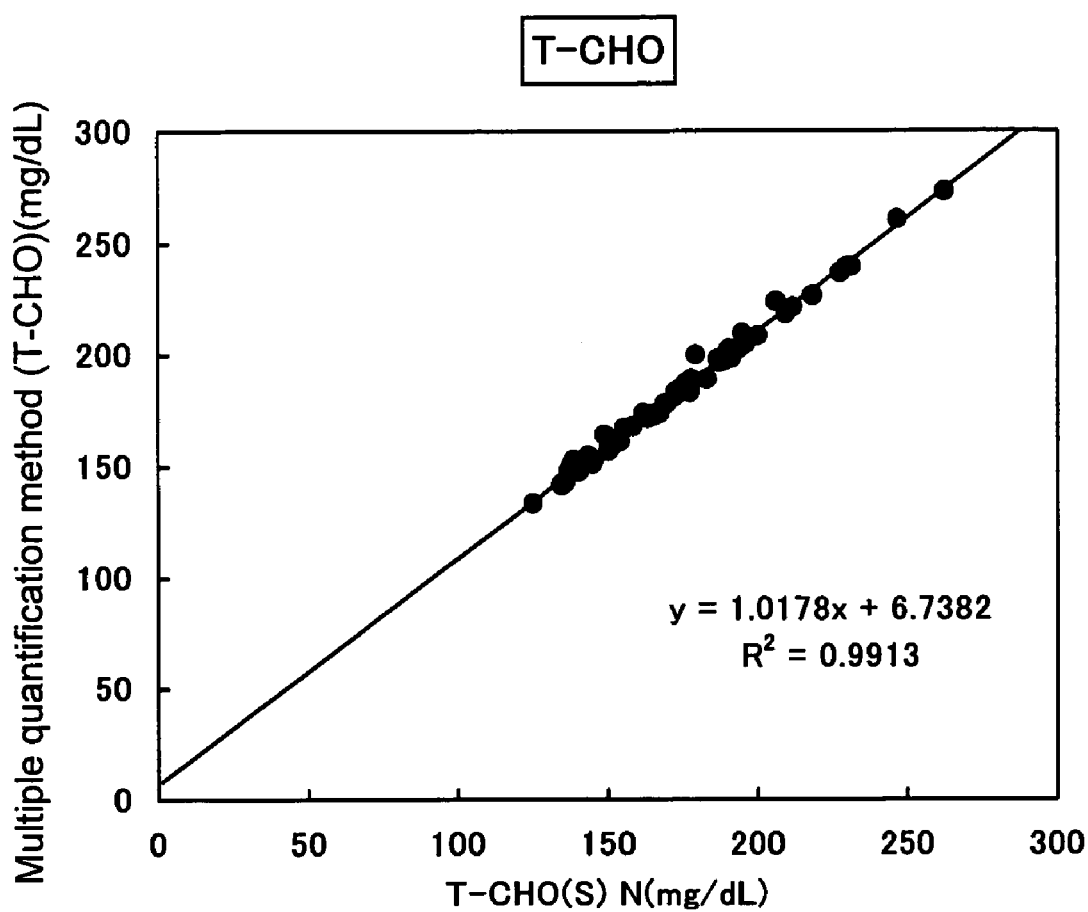
FIG. 3 is a diagram showing the correlation between total cholesterol levels measured by the method of multiple quantification of the present invention and total cholesterol levels measured independently.

The correlation between the measurement value of cholesterol in LDL measured with LDL-EX N that is a control product for evaluation and the measurement value measured by the method of the present invention is shown in FIG. 2. The correlation between the measurement value of total cholesterol measured with T-CHO(S)N that is a control product for evaluation and the measurement value measured by the method of the present invention is shown in FIG. 3. As shown in FIGS. 2 and 3, measurement results similar to values when LDL-C and T-CHO were each measured separately have been obtained by the simultaneous quantification of the present method.

All publications, patents, and patent applications cited in the present specification are incorporated by reference in their entireties into the present specification.

The invention claimed is:

1. A method of quantification for cholesterol in low density lipoprotein and total cholesterol simultaneously in a biological sample, comprising:
   (i) adding a first reagent in the biological sample such that hydrogen peroxide is generated from lipoproteins other than low density lipoprotein; and
   (ii) adding a second reagent to the biological sample of step (i) such that the hydrogen peroxide generated in step (i) is converted to a quinone dye and that additional hydrogen peroxide is generated from low density lipoprotein and converted to the quinone dye,
   wherein the quantity of cholesterol in low density lipoprotein and the quantity of total cholesterol are determined by readings of absorbance at different time points following addition of the second reagent.

2. The method of claim 1, wherein:
   (a) said first reagent comprises a surfactant that acts on lipoproteins other than low density lipoprotein, a cholesterol esterase, a cholesterol oxidase and a compound that is either 4-aminoantipyrine or a phenolic or anilinic hydrogen donor compound;
   (b) said first reagent does not comprise peroxidase; and
   (c) said second reagent comprises a surfactant that acts on low density lipoprotein, a cholesterol esterase, a cholesterol oxidase, peroxidase and a compound that is either 4-aminoantipyrine or a phenolic or anilinic hydrogen donor compound but different from the compound in the said first reagent.

3. The method of claim 1, wherein the first reading of absorbance is taken at 30 seconds after addition of said second reagent, and the second reading of absorbance is taken at 5 minutes after addition of said second reagent.

4. The method of claim 1, wherein the measurement is performed by an automatic analyzer for clinical chemistry testing.

* * * * *